US008147457B2

(12) United States Patent
Michael et al.

(10) Patent No.: US 8,147,457 B2
(45) Date of Patent: *Apr. 3, 2012

(54) CONICAL TROCAR SEAL

(75) Inventors: Cropper S. Michael, Edgewood, KY (US); Paul Franer, Cincinnati, OH (US); Thomas A. Gilker, Cincinnati, OH (US); Geoffrey C. Hueil, Mason, OH (US); David K. Norvell, Monroe, OH (US); Brian J. Thompson, Cincinnati, OH (US); Aaron C. Voegele, Loveland, OH (US); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1365 days.

This patent is subject to a terminal disclaimer.

(21) Appl. No.: 10/687,502

(22) Filed: Oct. 15, 2003

(65) Prior Publication Data

US 2007/0185453 A1    Aug. 9, 2007

Related U.S. Application Data

(60) Provisional application No. 60/456,386, filed on Mar. 21, 2003, provisional application No. 60/506,729, filed on Sep. 30, 2003, provisional application No. 60/506,730, filed on Sep. 30, 2003, provisional application No. 60/506,783, filed on Sep. 30, 2003, provisional application No. 60/506,786, filed on Sep. 30, 2003, provisional application No. 60/506,782, filed on Sep. 30, 2003, provisional application No. 60/506,725, filed on Sep. 30, 2003, provisional application No. 60/506,785, filed on Sep. 30, 2003, provisional application No. 60/506,737, filed on Sep. 30, 2003.

(51) Int. Cl.
*A61M 5/178* (2006.01)
(52) U.S. Cl. ................................................. 604/167.06
(58) Field of Classification Search ............. 604/167.06, 604/167.01, 167.02, 167.03, 167.07, 167.08, 604/167.11, 164.01, 164.02, 164.04, 164.03, 604/164.7, 164.08, 165.01
See application file for complete search history.

(56) References Cited

U.S. PATENT DOCUMENTS

| 3,504,699 A | 4/1970 | Grise |
| 3,773,233 A | 11/1973 | Souza |
| 4,436,519 A | 3/1984 | O'Neill |

(Continued)

FOREIGN PATENT DOCUMENTS

AU    2003203210 A1    1/2003

(Continued)

OTHER PUBLICATIONS

European Search Report dated Jun. 1, 2004, for corresponding EP application 04251605.4.

(Continued)

*Primary Examiner* — Jackie Ho
*Assistant Examiner* — Michael J Anderson (57) ABSTRACT

A trocar for performing a procedure on a patient. The trocar includes a hollow cannula having a distal end and a proximal end. The trocar includes a housing having a distal end attached to the proximal end of the cannula and a proximal end having a wall attached thereto. The wall having an aperture therethrough. The trocar further includes a first seal disposed within the housing comprising a plurality of layered elastomeric members forming conical shape.

15 Claims, 8 Drawing Sheets

U.S. PATENT DOCUMENTS

| | | | |
|---|---|---|---|
| 4,601,710 A | 7/1986 | Moll | |
| 4,610,665 A | 9/1986 | Matsumoto et al. | |
| 4,654,030 A | 3/1987 | Moll et al. | |
| 4,655,752 A | 4/1987 | Honkamen et al. | |
| 4,902,280 A | 2/1990 | Lander | |
| 4,931,042 A | 6/1990 | Holmes et al. | |
| 4,932,633 A | 6/1990 | Johnson et al. | |
| 5,030,206 A | 7/1991 | Lander | |
| 5,053,013 A | 10/1991 | Ensminger et al. | |
| 5,104,383 A * | 4/1992 | Shichman | 604/167.06 |
| 5,203,773 A | 4/1993 | Green | |
| 5,209,737 A | 5/1993 | Ritchart et al. | |
| 5,211,634 A | 5/1993 | Vaillancourt | |
| 5,246,425 A | 9/1993 | Hunsberger et al. | |
| 5,300,033 A | 4/1994 | Miller | |
| 5,308,336 A | 5/1994 | Hart et al. | |
| 5,324,270 A | 6/1994 | Kayan et al. | |
| 5,342,315 A * | 8/1994 | Rowe et al. | 604/167.06 |
| 5,364,372 A | 11/1994 | Danks et al. | |
| 5,366,445 A | 11/1994 | Haber et al. | |
| 5,385,552 A * | 1/1995 | Haber et al. | 604/167.03 |
| 5,385,553 A | 1/1995 | Hart et al. | |
| 5,441,041 A | 8/1995 | Sauer et al. | |
| 5,456,284 A | 10/1995 | Ryan et al. | |
| 5,467,762 A | 11/1995 | Sauer et al. | |
| 5,534,009 A | 7/1996 | Lander | |
| 5,542,931 A | 8/1996 | Gravener et al. | |
| 5,569,160 A | 10/1996 | Sauer et al. | |
| 5,578,016 A | 11/1996 | Zinger | |
| 5,584,850 A | 12/1996 | Hart et al. | |
| 5,603,702 A | 2/1997 | Smith et al. | |
| 5,628,732 A | 5/1997 | Antoon, Jr. et al. | |
| 5,643,301 A | 7/1997 | Mollenauer | |
| 5,662,615 A * | 9/1997 | Blake, III | 604/167.06 |
| 5,743,884 A | 4/1998 | Hasson et al. | |
| 5,792,113 A | 8/1998 | Kramer et al. | |
| 5,800,451 A | 9/1998 | Buess et al. | |
| 5,807,338 A | 9/1998 | Smith et al. | |
| 5,865,807 A * | 2/1999 | Blake, III | 604/167.06 |
| 5,895,377 A | 4/1999 | Smith et al. | |
| 6,017,356 A | 1/2000 | Frederick et al. | |
| 6,024,729 A | 2/2000 | Dehdashtian et al. | |
| 6,086,603 A | 7/2000 | Termin et al. | |
| 6,093,176 A | 7/2000 | Dennis | |
| 6,217,555 B1 * | 4/2001 | Hart et al. | 604/167.01 |
| 6,254,529 B1 | 7/2001 | Ouchi | |
| 6,277,100 B1 | 8/2001 | Raulerson et al. | |
| 6,302,852 B1 | 10/2001 | Fleming, III et al. | |
| 6,352,520 B1 | 3/2002 | Miyazaki | |
| 6,569,120 B1 | 5/2003 | Green et al. | |
| 6,610,031 B1 | 8/2003 | Chin | |
| 6,613,063 B1 | 9/2003 | Hunsberger | |
| 6,685,630 B2 | 2/2004 | Sauer et al. | |
| 6,702,787 B2 | 3/2004 | Racenet et al. | |
| 2002/0007152 A1 * | 1/2002 | Hermann et al. | 604/167.04 |
| 2002/0007153 A1 | 1/2002 | Wells et al. | |
| 2002/0010425 A1 | 1/2002 | Guo et al. | |
| 2002/0111585 A1 * | 8/2002 | Lafontaine | 604/167.06 |
| 2003/0040711 A1 * | 2/2003 | Racenet et al. | 604/167.06 |
| 2003/0050604 A1 * | 3/2003 | Lui et al. | 604/167.06 |
| 2003/0060770 A1 | 3/2003 | Wing et al. | |
| 2003/0109853 A1 * | 6/2003 | Harding et al. | 604/536 |
| 2003/0181858 A1 * | 9/2003 | Lajtai et al. | 604/167.06 |
| 2003/0187397 A1 | 10/2003 | Vitali | |
| 2004/0006356 A1 * | 1/2004 | Smith | 606/167 |
| 2004/0049173 A1 | 3/2004 | White et al. | |
| 2004/0059297 A1 * | 3/2004 | Racenet et al. | 604/167.06 |
| 2004/0064100 A1 | 4/2004 | Smith | |
| 2004/0111060 A1 | 6/2004 | Racenet | |
| 2004/0147949 A1 | 7/2004 | Stellon et al. | |
| 2004/0204682 A1 * | 10/2004 | Smith | 604/167.06 |
| 2004/0210194 A1 * | 10/2004 | Bonnette et al. | 604/167.06 |
| 2004/0230161 A1 * | 11/2004 | Zeiner | 604/167.06 |
| 2004/0260244 A1 * | 12/2004 | Piechowicz et al. | 604/167.06 |
| 2005/0020981 A1 * | 1/2005 | Kurth | 604/167.06 |
| 2005/0065475 A1 * | 3/2005 | Hart et al. | 604/167.06 |
| 2005/0096605 A1 * | 5/2005 | Green et al. | 604/246 |
| 2005/0131349 A1 * | 6/2005 | Albrecht et al. | 604/167.06 |
| 2005/0165356 A1 * | 7/2005 | Pasqualucci | 604/167.06 |
| 2005/0171479 A1 * | 8/2005 | Hruska et al. | 604/167.06 |
| 2005/0212221 A1 * | 9/2005 | Smith et al. | 277/628 |
| 2006/0041232 A1 * | 2/2006 | Stearns et al. | 604/167.06 |

FOREIGN PATENT DOCUMENTS

| | | |
|---|---|---|
| AU | 2004201173 B2 | 10/2004 |
| DE | 10100756 | 8/2002 |
| EP | 0568383 | 11/1993 |
| EP | 0696459 A1 | 2/1996 |
| EP | 0339945 | 11/1998 |
| EP | 1348386 A1 | 10/2003 |
| EP | 1459688 B1 | 9/2004 |
| JP | 06-007369 | 1/1994 |
| JP | 08-057056 | 3/1996 |
| JP | 2001-128985 | 5/2001 |
| WO | WO 94/03232 | 2/1994 |
| WO | WO 98/50093 A | 11/1998 |
| WO | WO/ 0035529 | 6/2000 |
| WO | WO2004/033004 | 4/2004 |

OTHER PUBLICATIONS

European Search Report dated Dec. 13, 2004 for corresponding EP application 04256023.

European Search Report dated Feb. 2, 2005 for corresponding EP application 04256016.

European Search Report dated Jul. 13, 2005 for corresponding EP application 05251974.

European Search Report dated Jun. 15, 2004, for corresponding EP application 042516054.

* cited by examiner

CONICAL TROCAR SEAL

This present application is a continuation in part of U.S. Patent Application Ser. No. 60/456,386, filed on Mar. 21, 2003, entitled: Improved Trocar Seal.

This application is related to the following copending and commonly assigned patent applications: application Ser. No. 60/506,729; entitled: Multi-Angled Duckbill Seal Assembly, filed on Sep. 30, 2003. Application Ser. No. 60/506,730, entitled: Reinforced Seal Assembly; filed on Sep. 30, 2003; application Ser. No. 60/506,783; entitled: Improved Trocar Housing/Stopcock Assembly, filed on Sep. 30, 2003; application Ser. No. 60/506,786; entitled: Rotational Latching System for Trocar, filed on Sep. 30, 2003; application Ser. No. 60/506,782; entitled: Woven Protector for Trocar Seal Assembly, filed on Sep. 30, 2003; application Ser. No. 60/506,725; entitled: Trocar Assembly Tip Protector, filed on Sep. 30, 2003; application Ser. No. 60/506,785; entitled: Low-Profile, Recessed Stopcock Valve for Trocar Assembly, filed on Sep. 30, 2003; application Ser. No. 60/506,737; entitled: Instrument Lock Assembly for Trocar, filed on Sep. 30, 2003; all of which are hereby incorporated herein by reference.

FIELD OF THE INVENTION

The present invention has application in conventional endoscopic and open surgical instrumentation as well application in robotic-assisted surgery. The present invention further relates to trocars to assist in performing minimally invasive surgery and, more particularly, to improved seals for such trocars.

BACKGROUND OF THE INVENTION

The use of endoscopic procedures in surgery has become widely accepted. The term endoscopic as used herein is defined to include all types of minimally invasive surgical procedures including laparoscopic and arthroscopic procedures. Accordingly, numerous endoscopic instruments have been developed which allow the surgeon to perform complex surgical procedures with minimal incisions into the skin and tissue surrounding a particular body cavity or anatomical region. In order to introduce the endoscopic instrumentation into the body cavity, it is often necessary to puncture and cannulate the body cavity by using a trocar. Trocars are widely known in the art and typically consist of an obturator and a trocar cannula. An example of a trocar can be found in U.S. Pat. No. 6,017,356 issued to Frederick et al. on Jan. 25, 2000, which is hereby incorporated herein by reference.

It is common for a sealing arrangement or sealing device to be used in association with the cannula to prevent the escape of fluid or gas during endoscopic procedures. During an endoscopic surgical procedure, the internal gas pressure must be maintained in order to successfully complete the procedure. In order to maintain the internal gas pressure while instruments are passed into and out of the trocars positioned in a body cavity, sealing devices are required for both the instruments and for the trocar assemblies. That is most trocars have two sealing devices. One which seals the trocar when there is not an instrument passing therethrough, and one which seals the trocar as instruments are passed therethrough. Furthermore, it is desirable that the sealing device maintain gas pressure in the abdominal cavity, despite numerous insertions and withdrawals of surgical instruments through the trocar cannula.

Most commercially available trocars have an outer seal and an inner seal. The outer seal is typically a gasket located at the proximal most end of the trocar cannula. This gasket tightly fits itself around the elongated shafts of any medical devices passing therethrough. Therefore, the outer seal prevents fluids from escaping the body cavity through the trocar cannula while surgical instruments are being used with the cannula. The inner seal is typically what is referred to as a flapper door. It is made from a rigid, typically plastic, door which is spring biased against an inner gasket. The inner seal prevents fluids from escaping the body cavity through the trocar cannula while the trocar cannula is not in use, i.e. with no surgical instruments or obturators passing therethrough. The inner seal is located with the trocar cannula handle, distal to the outer seal.

The present invention provides for an improved outer seal.

SUMMARY OF THE INVENTION

A trocar for performing a procedure on a patient. The trocar includes a hollow cannula having a distal end and a proximal end. The trocar includes a housing having a distal end attached to the proximal end of the cannula and a proximal end having a wall attached thereto. The wall having an aperture therethrough. The trocar further includes a first seal disposed within the housing comprising a plurality of layered elastomeric members forming conical shape.

DETAILED DESCRIPTION OF THE DRAWINGS

Figure 1:
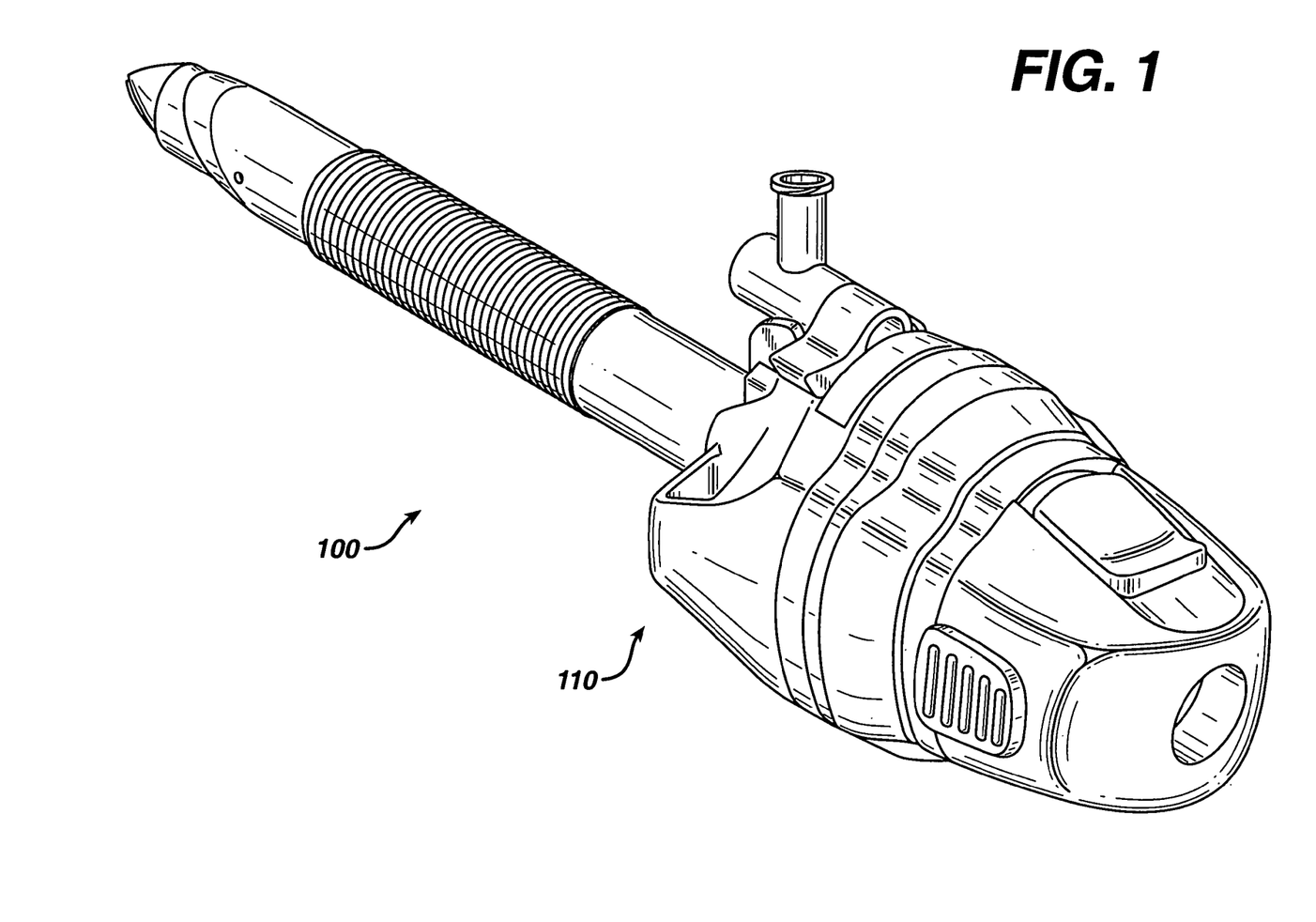
FIG. 1 is a perspective view of a trocar in accordance with the present invention.

Referring now to the drawings wherein like numerals indicate the same elements throughout the views, there is shown in FIG. 1 a trocar, 100 in accordance with the present invention. Trocar 100 can be similar to the one described in U.S. Pat. No. 6,017,356 issued to Fredrick et al, which is herein incorporated by reference. Trocar 100 comprises of cannula portion 110 and obturator portion 120. The obturator portion is well known to those skilled in the art, and can be bladed and non-bladed such as those available on the ENDOPATH II® Trocar sold by Ethicon Endo-Surgery, Cincinnati, Ohio. Obturator portion 120 has a piercing tip 122 which is used to pierce the patients tissue until it reaches the abdominal cavity. After penetration into the abdominal cavity is complete, obturator portion 120 can be removed from cannula portion 110. After the obturator portion is removed, any number of surgical instruments such as, for example, a tissue fastening instrument can be inserted through the cannula of the trocar to perform the surgical procedure.

Figure 7:
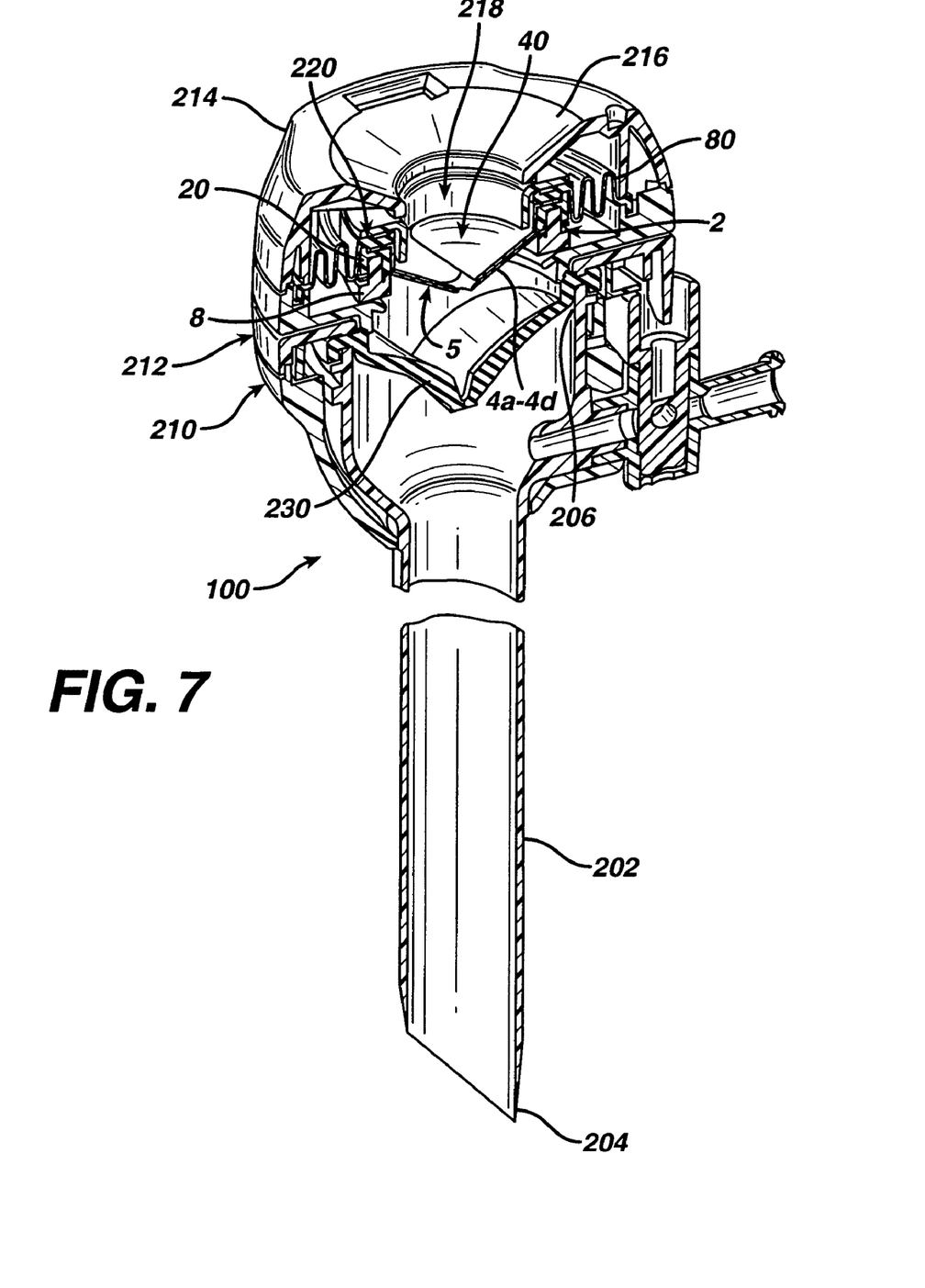
FIG. 7 is a cross-sectional view of trocar 100 shown in FIG. 1, taken along line 7-7 and having the obturator 110 removed for clarity.

As seen from FIG. 7, a preferred embodiment of the present invention is a trocar 100 for performing a procedure on a patient. Trocar 100 includes a hollow cannula 202 having a distal end 204 and a proximal end 206. Trocar 100 also includes a housing 210 having a distal end 212 attached to the proximal end 206 of the cannula 202 and a proximal end 214 having a wall 216 attached thereto, the wall having an aperture 218 extending therethrough. Trocar 100 includes a seal assembly 2 disposed within the housing comprising a plurality of layered elastomeric members 4a-4d forming conical shape seal 5. As described below, the plurality of layered elastomeric members 4a-4d preferably have a semi-circular profile, and preferably having a circumference of about 180 to 270 degrees. As described below, the seal assembly preferably includes a first and second rigid rings (gasket retainer ring 8 and gasket ring 20) wherein the layered elastomeric members 4a-4d are disposed between and are abutting against the rings 8 and 20. As described below, the elastomeric members 4a-4d preferably include a proximal flange portion 70, and an inwardly extending portion 72 extending distally therefrom, wherein the proximal flange portions are disposed between and are abutting against the rings. Preferably, the seal assembly 2 has an outer perimeter 220 which is attached to a flotation means 80. As will be described in greater detail below, seal assembly 2 preferably includes a plurality of protectors 40 disposed proximal to the elastomeric seal. Lastly, trocar 100 preferably includes a zero closure valve shown in FIG. 7 as a duck bill valve 230.

Figure 2:
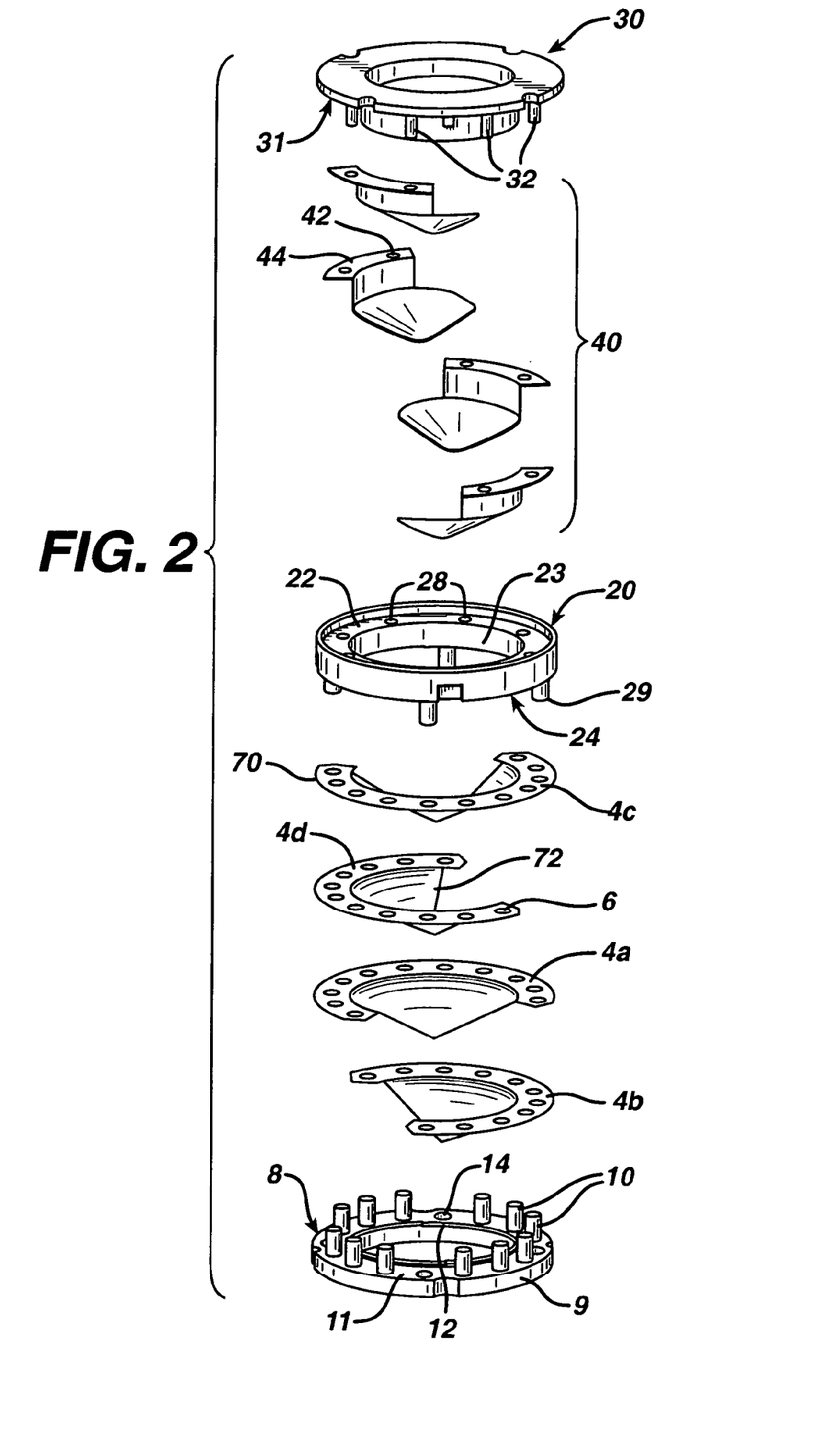
FIG. 2 is an exploded view of the seal assembly 2 of the present invention.
Figure 2A:
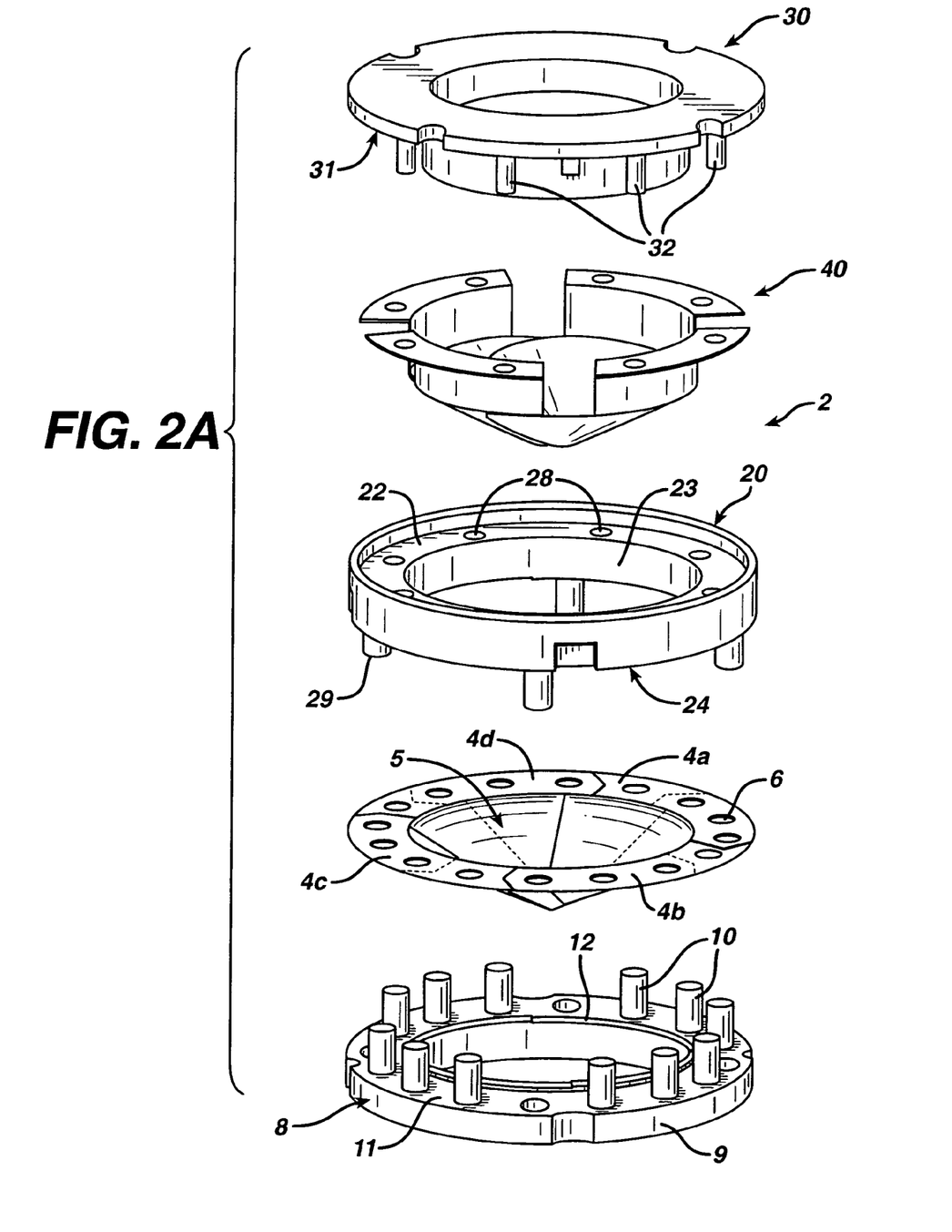
FIG. 2A, is a view similar to that of FIG. 2 but showing the protector segments 40 and seal segments 4a-4d assembled in a preferred embodiment.

Referring now to FIGS. 2 and 2A, there is shown seal assembly 2 made in accordance with the present invention. Seal assembly 2 a crown 30, protectors 40, gasket ring 20, seal segments 4a-4d and gasket retainer ring 8. Gasket retainer ring 8 can be made of any number of materials known to those skilled in the art including, but not limited to, polycarbonate. Gasket retainer ring 8 includes ring base 9 having a top 11. Extending from top 11 of ring base 9 is a plurality of retainer pins 10. Ring base 9 also includes a plurality of holes 14 extending therethrough. Retainer pins 10 can be attached to top 11 of ring base 9 by any attachment means known to those skilled in the art or can integrally molded with ring base 9. Retainer pins 10 can be used with seal segments 4a-4d by placing the gasket retainer holes 6 over retainer pins 10. Ring base 9 further includes crush rib 12, shown in FIG. 2A. Crush rib 12, which is the inner edge of the opening of ring base 9.

Figure 4:
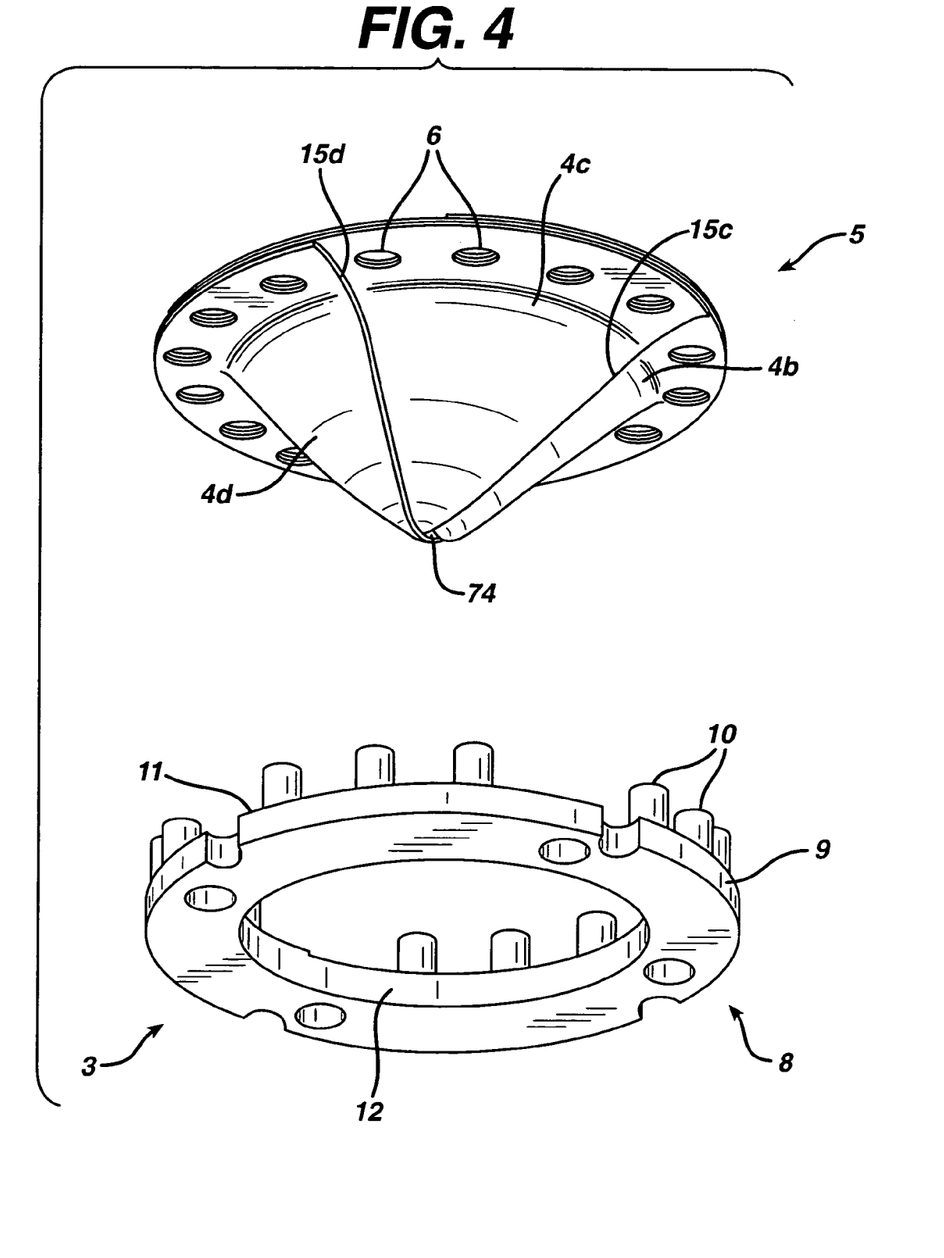
FIG. 4 is a perspective view of the retainer ring assembly 20 used in the present invention and seal segments 4a-4d separated for clarity.

Gasket ring 20, shown in FIG. 4, helps in securing seal segments 4a-4d onto retainer ring 8. Gasket ring 20 can be made of any number of materials known to those skilled in the art including, but not limited to, polycarbonate. Gasket ring 20, has top 22, bottom 24, and opening 23 therethrough. Gasket ring 20 further includes a plurality of gasket pin holes (not shown) disposed therein on bottom 24 for receiving retainer pins 10 and a plurality of crown holes 28 therein on top 22 for receiving crown pins 32. Gasket ring 20 further includes a plurality of gasket pins 29 extending from bottom 24.

As shown in FIG. 2, the seal assembly 2 further includes crown ring 30 and a plurality of protectors 40, which are located over seal segments 4a-4d. Crown ring 30, which can be made of any number of materials known to those skilled in the art including, but not limited to polycarbonate, is ring shaped member having bottom 31. Extending from bottom 31 of crown ring 30 is a plurality of crown pins 32. Crown pins 32 can be attached to bottom 31 of crown ring 30 by any attachment means known to those skilled in the art or can integrally molded therewith. Crown pins 32 can be used to assemble protectors 40 to gasket ring 20 of gasket assembly 3 forming seal assembly 2 of the present invention as illustrated in FIG. 2. Protectors 40, which are preferably made of a thin flexible polymer, can be slightly trapezoidal and are overlapped or woven with one another and attached together by any means known to those skilled in the art to form a conical shape as illustrated in FIG. 2. Such protectors are further described in the above incorporated reference application Ser. No. 60/506,782, titled WOVEN PROTECTOR FOR TROCAR SEAL ASSEMBLY, filed on Sep. 30, 2003.

The protectors 40 are attached to seal assembly 2 by trapping them between the distal surface 31 of the crown ring 30 and the proximal surface 22 of the gasket ring 20. Crown pins 32 on the distal surface 31 of the crown ring 30 pass through protector holes 42 in the protector flange 44 of the protectors 40. These crown pins 32 also affix to crown holes 28 on the proximal surface 22 of the gasket ring 20, thereby holding the protectors 40 fixed in place between the surfaces of the two parts.

When assembled as seal assembly 2, the protectors are layered together as described above, and the seal segments are layered together as described below. As is better seen by referring to FIG. 3, gasket pins 10 go through holes 6 in seal segments 4, and snap into gasket pin holes 26, and gasket pins 29 snap into holes 14 on retainer ring 8 to secure gasket ring 20 to gasket retainer ring 8 together, with the seal segments disposed therebetween. Crown pins 32 go through holes 42 on protectors 40 and snap into crown holes 28 to help secure gasket ring 20 to crown 30 with protectors 40 disposed therebetween. When all assembled, it forms seal assembly 2 (shown in FIG. 7).

Seal protectors 40 are well known in the art and are described in U.S. Pat. No. 5,308,336 issued to Hart et al. on May 3, 1994, which is hereby incorporated herein by reference. As illustrated in FIGS. 2-6, retainer ring assembly 3 includes four seal segments 4a-4d, gasket retainer ring 8, and gasket ring 20. Any number of seal segments can be used and the invention herein is not limited by four. Each seal segment 4a-4d, which can be made of but is not limited to an elastomer such as, for example, silicon, can be molded flat or non-planer.

In one alternate embodiment, the pins and hole combinations are split between the gasket retainer ring 8 and the gasket ring 20. Four pins and twelve holes can be integral to the gasket ring 20, and twelve pins and four holes can be integral to the gasket retainer ring 8. The seals are then "woven" onto the gasket ring 20, requiring placement of each seal segment over only 3 pins. This is compared to the 10 pins required in the embodiment previously described. These pins hold the seal in the proper configuration, providing alignment of the gasket holes 6 with the remaining pin-hole pairs (10 and 26). When the gasket retainer ring 8 is assembled to the gasket ring 20, the twelve pins on the gasket retainer ring pass through the aligned gasket holes, thereby trapping the seals as in the previous embodiment. Any number or combinations of pins and holes on gasket members 8 and 20 can be used.

Alternatively, one can use only four pins are for positive fixation through the gasket holes (6). The four pins can be located the gasket ring 20 and four corresponding holes can be located on the gasket retainer ring. The seal segments (4a-d) have holes only corresponding to these locations. To supplement the fixation associated with these pin-hole combinations, additional "pinch-pins" can be located on both the gasket ring 20 and the gasket retainer ring 8. These pinch-pins are conical-shaped protrusions projecting from both the distal surface 24 of the gasket ring 20 and the proximal surface 11 of the gasket retainer ring 8. These conical protrusions on each part radially align with one another, and compress the perimeter flange of the seal segments when the gasket ring 20 and gasket retainer ring 8 are assembled together. Due to the sharpness of the tip on the conical protrusions, they "dig in" to the flexible material of the seal segments, aiding in fixation of the perimeter of the seal segments.

Figure 5:
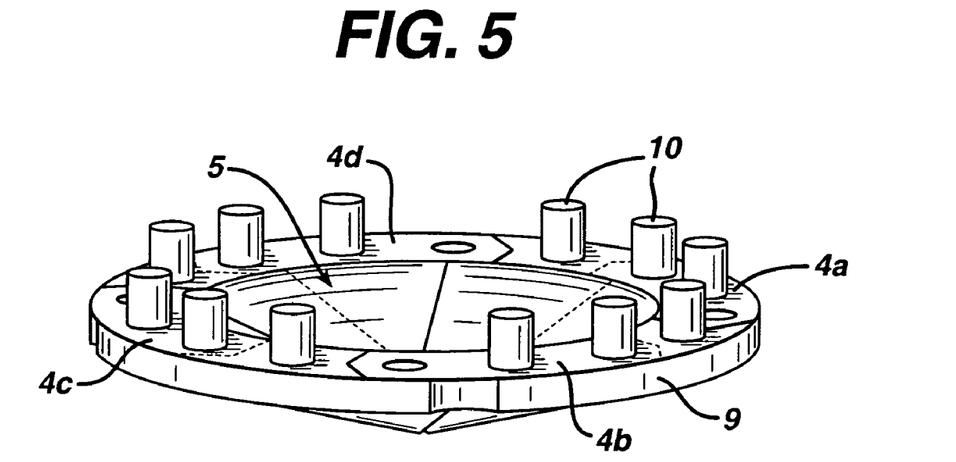
FIG. 5 is a perspective view showing seal 5 of the present invention.

Seal segments 4 can be made from any number of materials known to those skilled in the art including polyisoprene and silicone. Seal segments 4 comprise a proximal flat flange portion 70, and a inwardly extending distal portion 72. Seal segments 4, as seen in FIG. 2, can have a semicircular shape having a circumference of 225 degrees such that when they are layered together they have a conical shape as shown in FIG. 5. However, any number of different shapes would work as well. The seal segments can also be molded non-planer and each segment can be identical in design and shape or different. Preferably, the seal assembly 2 of the present inventions includes a plurality of seal segments 4 which are layered so as to form a multi-layer conical seal 5. The seal segments 4 can be stacked on top of one another to form this layered configuration, or can be woven together as described below.

Figure 3:
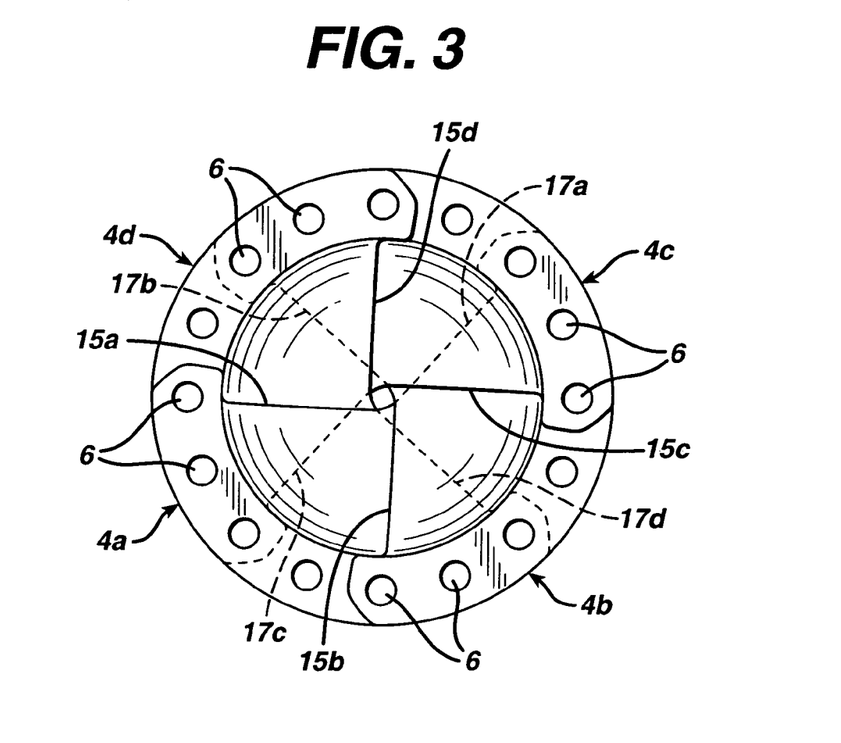
FIG. 3 is a plan view of the seal segments 4(a)-4(d) used in the seal 5 of the present invention.

In one preferred embodiment, as best described by referring to FIGS. 3, 4 and 5, seal segments 4a-4d are woven with one another. Now, it will be described how seal segments 4a-4d can be assembled with retainer ring 8 and gasket ring 20 to form conical seal 5 of the present invention. The assembly can be completed by first placing gasket holes 6 of first seal segment 4a onto gasket retainer pins 10 of gasket retainer ring 8 as shown in the figures. Since first seal segment 4a is the first seal to be assembled to retainer ring 8 there is no specific retainer pin 10 location necessary to place gasket holes 6 of first seal 4a thereover. The gasket holes 6 of second seal segment 4b are then positioned onto gasket retainer pins 10 of gasket retainer ring 8 such that starting edge 15b of second seal 4b overlaps ending edge 17a of first seal 4a. Basically, the starting edge of each seal segment will share at least one retainer pin of the ending edge of an adjacent seal segment such that the starting edge of one seal segment will be overlapped on top of the ending edge of an adjacent seal segment. Since this is a four piece design, starting edge 15b of second seal segment 4b is located at a position 90 degrees, in a counter clockwise fashion, from the starting edge 15a of the first seal segment 4a. After third section 4c has been placed on the pins, starting edge 15a of first seal segment 4a is removed from the pins allowing ending edge 17d of fourth seal segment 4d to be placed thereunder such that all seal segments 4a-4d are overlapping as shown in FIGS. 3-4. Staring edge 15d of fourth seal segment 4d is placed on gasket retainer pins 8 in the same manner as the others over third seal segment 4c. However, ending edge 17d of fourth seal segment 4d is placed under the removed portion of starting edge 15a of first seal segment 4a. Once fourth seal segment 4d has been seated on all of the gasket retainer pins 8, the removed portion of the first seal segment 4a is placed over the ending portion of the fourth seal segment 4d.

The above described embodiment of placing seal segments 4a-4d onto retainer pins 10, allows seal segments 4a-4b to form a seal 5 having a conical shape as shown in FIGS. 3 and 5. FIG. 5 shows seal 45 as having a hole 74 at its distal end. However, seal segments 4 could be configured so as not to have a hole therethrough so as to form a zero closure valve. In addition, the seal segments themselves can be molded such that they have a varying thickness across the profile of the seal. This can be done for several reasons i.e. minimizing leak rate, drag, and is also described in the above incorporated reference Ser. No. 60/506,730 titled REINFORCED SEAL ASSEMBLY, filed on Sep. 30, 2003.

Figure 6:
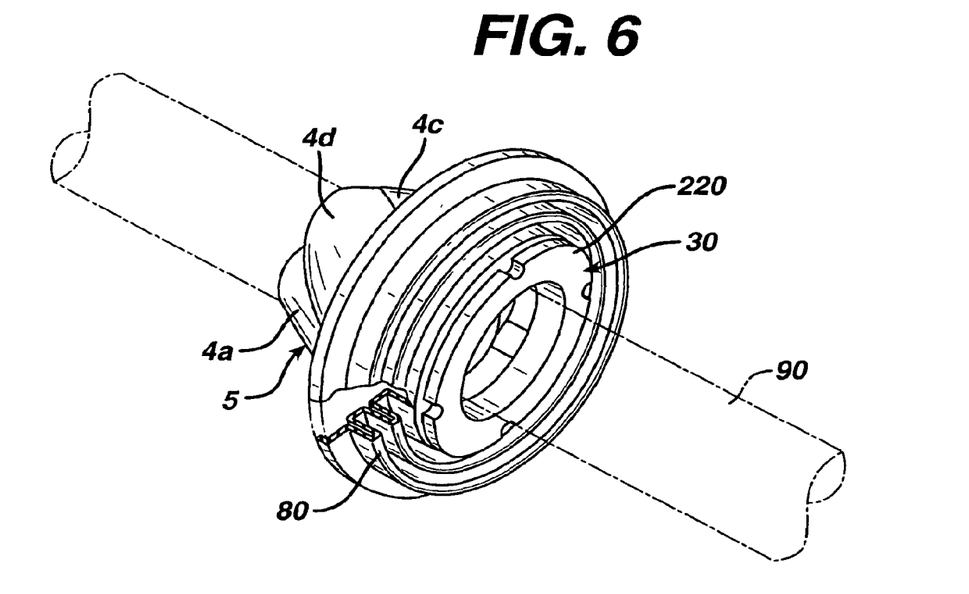
FIG. 6 is a perspective view of seal 5, attached to a flotation system 80 having an instrument 90 inserted therethrough.

Referring to FIG. 6, a benefit of seal assembly 2 of the present invention is illustrated showing an increase in the ability to a insert surgical instrument 90, like a surgical stapler or clip applier, with a larger range of instrument shaft diameters 50 into a trocar of the type described above as item 100. The herein described seal eliminates the classical issue of "hoop-stress" associated with lip seals. By breaking the seal into multiple segments, the strain in the system can be greatly reduced during instrument insertion. In the case of a seal that must seal on both 5 mm instruments as well as 12 mm instruments, this reduction in strain is believed to be as much as 75%. This yields much lower peak instrument insertion forces, instrument insertion drag forces, instrument extraction drag forces, and instrument peak extraction forces. The reduction in strain allows the seal to resist puncture during insertion of sharp instruments better than lip seals. When a sharp instrument contacts the seal, the increase in strain does not occur as rapidly as in lip seals. This allows the instrument to pass by prior to critical strain levels being reached, resulting in a puncture or tear.

The interwoven design of the seals of the above described embodiment allows for a single thickness of one seal segment to be contacting the instrument during instrument use the majority of the time (sometimes the overlap allows two seal segments to be contacting the instrument in localized regions). This is unlike other segmented seals where multiple seal layers are required to be in contact with the instrument at a given location to provide an adequate seal. Therefore, the interwoven design provides a performance edge over other segments seal designs. This is evident in all areas of force associated with instrument use.

In addition, because the described embodiment reduces strain, it is possible to make the hole at the center of the seal smaller than is typically desired for lip seals. Forces associated with instrument use in lip seal designs are greatly affected by reductions in the size of the hole. While there is some impact with the segmented seal design of this patent, the effect is much less dramatic. Therefore, by reducing the hole-size at the center, the segmented seal can gain an improved ability to maintain insulflation when a small instrument is axially offset to one side of the trocar channel with a very minimal effect on instrument usage forces. Alternatively, the seal can be put together such that there is no hole present provides a zero-closure design, sealing both when no instrument is present and while an instrument is present.

Preferably, the seal assembly can be mounted onto the trocar through a flotation means or system such as a bellows. Such seal flotation systems are described in U.S. Pat. No. 5,385,553 issued to Hart et al. on Jan. 31, 1995, which is hereby incorporated herein by reference. By referring to FIG. 7, it can be seen that seal assembly 2 is connected to a flotation system 80. The bellows 80 allows for radial movement of the seal assembly. The radial force required to deflect the bellows radially is much less than the contact force exerted by the on the instrument. This will allow the flotation system to deflect while the seal segments maintain a sealing condition with the instrument. Protector flange 44 is first laid on top of ring surface 22. The flotation means can have a flange on its inner diameter with holes in it which can be laid over the protectors' flanges such that the holes in the bellow's flange line up with the holes in the protectors 42. This results in the flotation means being in-between, or sandwiched between, ring 31 and protectors 44. The flotation system can help to prevent the protectors from moving up and down unintentionally.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein have equal application in robotic-assisted surgery. In addition, it should be understood that every structure described above has a function and such structure can be referred to as a means for performing that function. Accordingly, it is intended that the invention be limited only by the spirit and scope of the appended claims.

What is claimed is:

1. A surgical access device, comprising a seal assembly having a plurality of separate semicircular seal segments arranged in a conical shape, each seal segment having a circumference greater than 180 degrees and being adapted to seal against objects positioned through the seal; and a zero closure seal spaced from and aligned with the seal segments.

2. The surgical access device of claim 1 wherein said seal assembly has an outer perimeter which is attached to a flotation means.

3. The surgical access device of claim 1 wherein said seal assembly includes a plurality of protectors disposed proximal to said plurality of separate semicircular seal segments.

4. The surgical access device of claim 1 wherein said plurality of separate semicircular seal segments are disposed such that there is a substantially centrally located aperture in said seal assembly.

5. The surgical access device of claim 1, further comprising a cannula.

6. A trocar for performing a procedure on a patient, said trocar comprising:
   a. a hollow cannula having a distal end and a proximal end;
   b. a housing having a distal end attached to said proximal end of said cannula and a proximal end having a wall attached thereto, said wall having an aperture therethrough;
   c. a seal assembly disposed within said housing comprising a first substantially rigid ring, a second substantially rigid ring, and a plurality of semicircular elastomeric members compressed therebetween and forming a conical shape, the elastomeric members circumscribing an aperture in an interwoven pattern and cooperate to sufficiently seal against objects positioned within the aperture to maintain gas pressure in the abdominal cavity during endoscopic surgical procedures; and wherein the seal assembly further comprises a zero closure seal disposed distally of the plurality of semicircular elastomeric members.

7. The trocar according to claim 6 wherein said elastomeric members comprise a proximal flange portion, and an inwardly extending portion extending distally therefrom, wherein said proximal flange portions are disposed between and are abutting against said rings.

8. The trocar according to claim 6 wherein said plurality of elastomeric layers are interwoven.

9. The trocar according to claim 6 wherein said plurality of elastomeric members have a non-planar shape prior to be assembled together.

10. A trocar for performing a procedure on a patient, said trocar comprising:
    a. a hollow cannula having a distal end and a proximal end;
    b. a housing having a distal end attached to said proximal end of said cannula and a proximal end having a wall attached thereto, said wall having an aperture therethrough;
    c. an instrument seal assembly disposed within said housing comprising a plurality of layered elastomeric members arranged circumferentially about an aperture in an alternating over and under pattern and forming a conical shape, the plurality layered elastomeric members cooperating to provide a substantially gas-tight seal against instruments positioned through the aperture; and wherein the instrument seal assembly further provides a zero-closure seal spaced from the plurality of layered elastomeric members arranged about the aperture.

11. The seal of claim 10, wherein the elastomeric members are semicircular.

12. The seal of claim 11, wherein the elastomeric members have a circumference between 180 to 270 degrees.

13. The seal of claim 10, wherein the elastomeric members are arranged in non-planar shape.

14. The seal of claim 10, wherein the instrument seal assembly comprises four elastomeric members.

15. The seal of claim 10, further comprising a first substantially rigid ring and a second substantially rigid ring, the elastomeric members being compressed therebetween.

* * * * *